United States Patent
Bak et al.

(10) Patent No.: US 7,348,476 B2
(45) Date of Patent: Mar. 25, 2008

(54) *SYNGONANTHUS CHRYSANTHUS* PLANT NAMED 'MIKADO'

(75) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 448 days.

(21) Appl. No.: 10/463,582

(22) Filed: Jun. 18, 2003

(65) Prior Publication Data

US 2004/0088769 A1 May 6, 2004

Related U.S. Application Data

(60) Provisional application No. 60/389,290, filed on Jun. 18, 2002.

(30) Foreign Application Priority Data

Jun. 18, 2001 (QZ) .................... PBR 20010955

(51) Int. Cl.
*A01H 5/00* (2006.01)

(52) U.S. Cl. ....................................... 800/323; 800/260
(58) Field of Classification Search ................... Plt./263
See application file for complete search history.

(56) References Cited

PUBLICATIONS

Moldenke, H. Notes on new and noteworthy plants. LVIII, Phytologia, 1973, pp. 430–432.*

* cited by examiner

*Primary Examiner*—Anne Kubelik
*Assistant Examiner*—June Hwu
(74) *Attorney, Agent, or Firm*—Foley & Lardner, LLP

(57) ABSTRACT

*Syngonanthus chrysanthus* culivar 'Mikado' is solid, tenable, small-sized, long-lasting plants; several single head, green-white inflorescences; well-suited for smaller pot sizes, 9 to 12 cm; year-round flowering, approximately 40–45 weeks after sowing.

5 Claims, 2 Drawing Sheets

(2 of 2 Drawing Sheet(s) Filed in Color)

SYNGONANTHUS CHRYSANTHUS PLANT NAMED 'MIKADO'

This application is based on U.S. provisional application Ser. No. 60/289,290 filed Jun. 18, 2002.

FIELD OF THE INVENTION

The present invention relates to a new, distinct and stable plant of *Syngonanthus chrysanthus* hereinafter referred to as 'Mikado.' The present invention relates to seeds which are *Syngonanthus chrysanthus* cultivar 'Mikado,' as well as the plants and plant parts produced from these seeds which have all the morphological and physiological characteristics of the *S. chrysanthus* cultivar 'Mikado.' The present invention also relates to methods for producing these seeds and plants. Furthermore, the present invention relates to a method of producing progeny *S. chrysanthus* plants by crossing *S. chrysanthus* cultivar 'Mikado,' as the male or female plant, with another *S. chrysanthus* plant and selecting progeny.

BACKGROUND OF THE INVENTION

*S. chrysanthus* is a member of the Eriocaulaceae family. The family is recognizable by its capitula of small button-like white, gray, brown or black flowers, atop tall stalks. *S. chrysanthus* plants grow natively as tropical, swamp plants and therefore this species grows best under humid conditions.

There are no known comparison cultivars to 'Mikado.' A need exists for varieties of *S. chrysanthus* cultivars with attractive ornamental features. Additionally, a need exists for *S. chrysanthus* cultivars that can be easily propagated by seed. The new cultivar was developed through a controlled breeding program and exhibits unique, desirable and stable characteristics.

SUMMARY OF THE INVENTION

The instant invention provides *S. chrysanthus* 'Mikado' plant selections that are solid, tenable, small-sized and long-lasting. The instant invention also provides *S. chrysanthus* 'Mikado' plant selections with several, single-head, green-white inflorescences.

These and other objectives have been achieved in accordance with the present invention which provides a new cultivar 'Mikado' that is a product of a planned breeding program undertaken by the inventors in Assendelft, The Netherlands, in 1999.

Seeds which are cultivar 'Mikado' were deposited with the American Type Culture Collection, 10801 University Boulevard, Manassas, Va. 20110-2209, and accorded Deposit Accession No. PTA-4765.

OBJECTS OF THE INVENTION

This invention relates to seeds which produce *S. chrysanthus* 'Mikado.' This invention also relates to *S. chrysanthus* plants, and parts thereof, having all the physiological and morphological characteristics of *S. chrysanthus* 'Mikado.' This invention also relates to plant parts, such as pollen, seeds or inflorescence produced by *S. chrysanthus* 'Mikado.'

This invention relates to a method of producing plants having all the physiological and morphological characteristics of the *S. chrysanthus* 'Mikado' comprising the steps of (a) crossing *S. chrysanthus* 'Mikado' produced from seed accorded ATCC accession no. PTA-4765 as a male or female parent with another *S. chrysanthus* plant and (b) selecting progeny.

BRIEF DESCRIPTION OF THE DRAWINGS

The file contains at least one drawing executed in color. Copies of this patent with the color drawing(s) will be provided by the Patent and Trademark Office upon request and payment of the necessary fee.

DETAILED DESCRIPTION OF THE PREFERRED EMBODIMENTS

Figure 1:
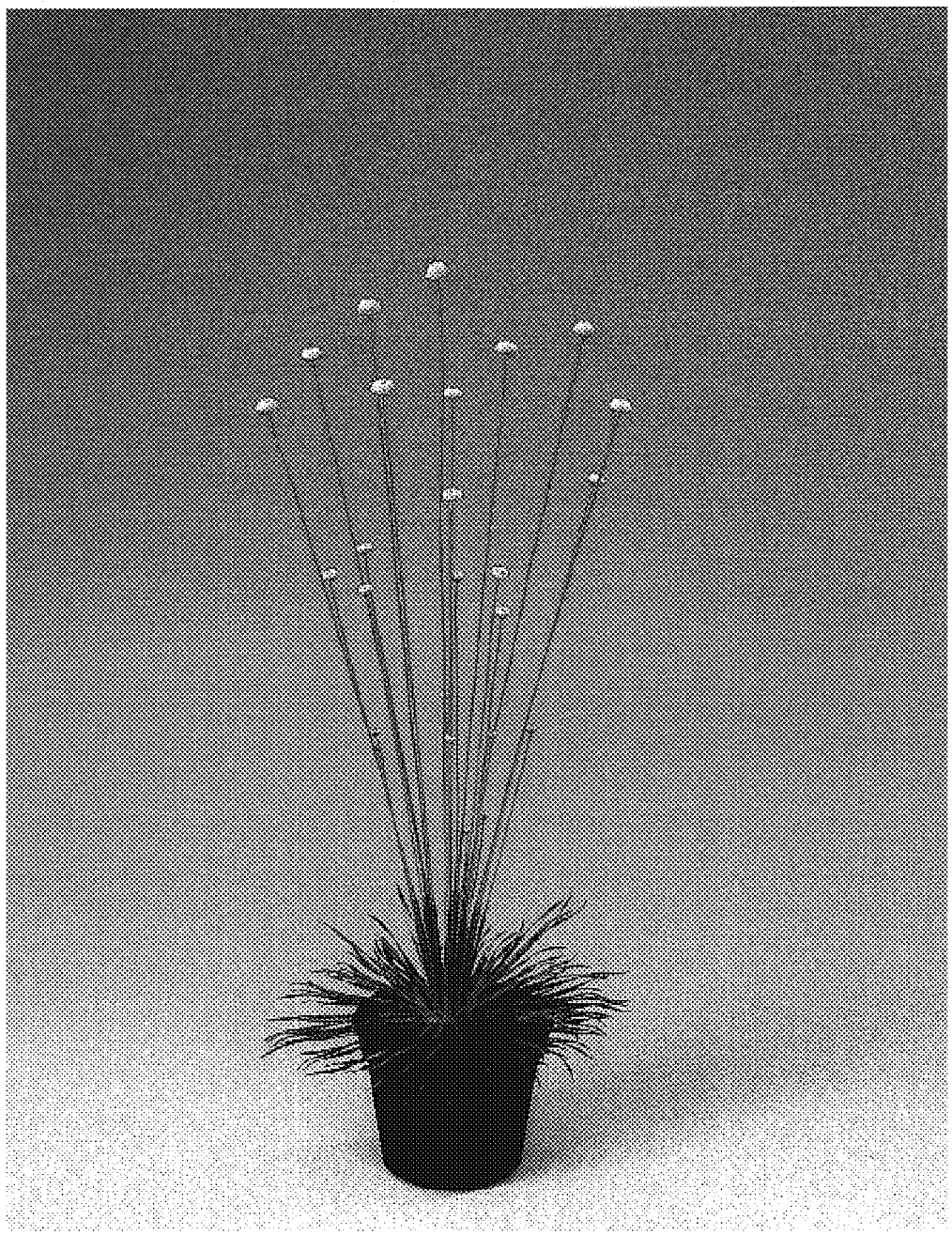
FIG. 1 shows the new cultivar 'Mikado' in its entirety. The photograph shows a whole plant side-view of the inflorescences and foliage.
Figure 2:
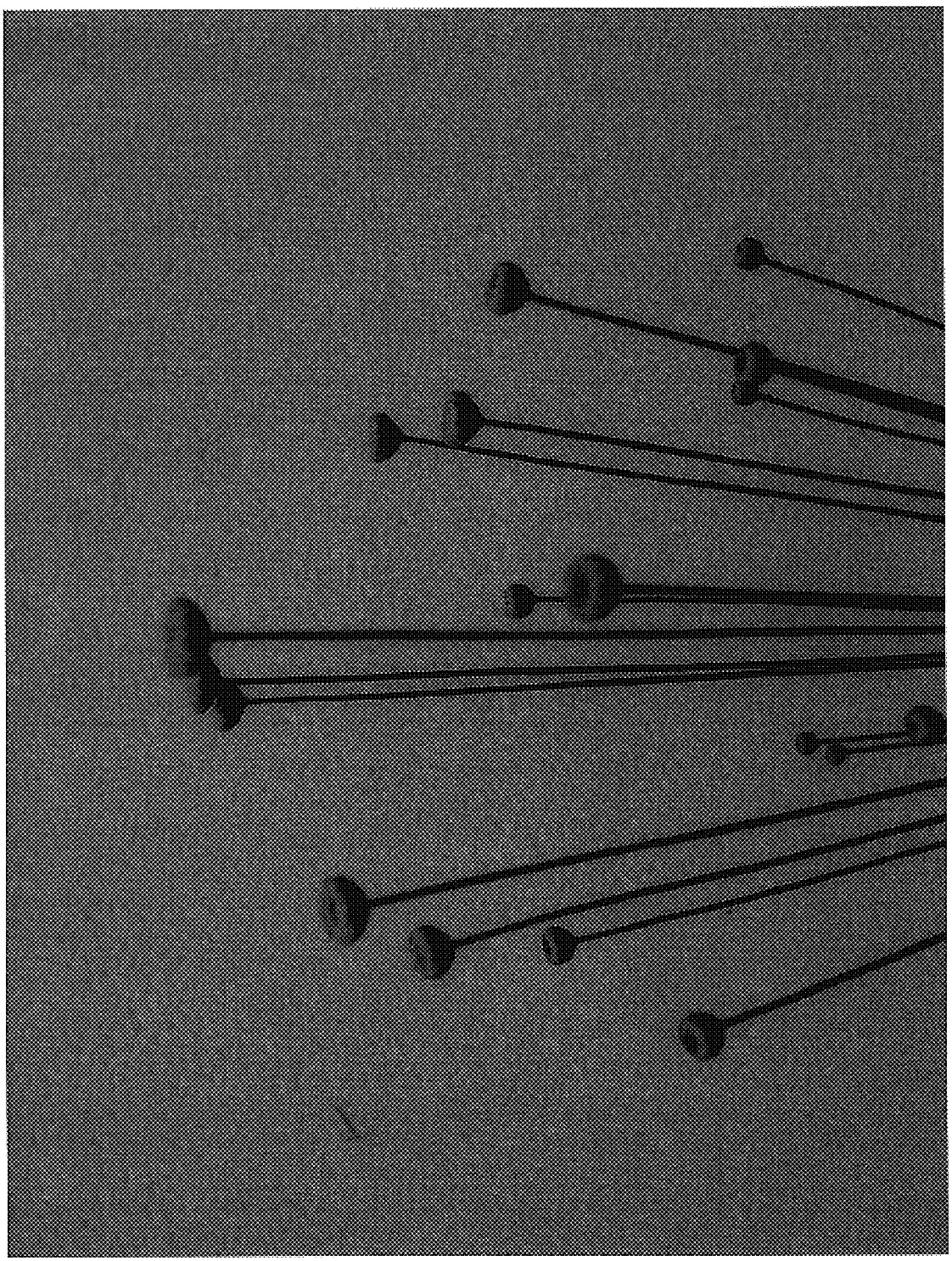
FIG. 2 shows a close-up of the pin-head flower buds of 'Mikado.'

The present invention was created by the inventors, Elly Bak and Nicolaas D. M. Steur, in 1999 and flowered for the first time in 2001 in Assendelft, The Netherlands.

'Mikado' is particularly characterized by the following characteristics:
1. solid, tenable, small-sized, long-lasting plants;
2. several single head, green-white inflorescences;
3. well-suited for smaller pot sizes, 9 to 12 cm;
4. year-round flowering, approximately 40–45 weeks after sowing.

The following characteristics are firmly fixed and retained through successive generations of asexual or sexual reproduction:

Reproduction of the cultivar is done by seed.

'Mikado' grows best at temperatures of 20–22° C. and a relative air humidity of 70%. 'Mikado' is well-suited for smaller pot sizes, or 9 to 12 cm in diameter. Keeping the pot moist is essential for healthy growth. The new cultivar flowers year-round, approximately 40–45 weeks after sowing.

'Mikado' has not been tested under all available environmental conditions. The phenotype may vary with variations in environmental conditions such as temperature, light intensity, frequency of fertilization, composition of fertilizer, acetylene treatment, day length, and humidity, without, however, any change in the genotype of the new cultivar.

There are no known comparison cultivars.

In the following description, color references are made to The Royal Horticultural Society Colour Chart (R.H.S.), except where general colors of ordinary significance are referred to.

Plant:
    *Form.*—Rosette.
    *Height.*—Approximately 23–36 cm (flowering).
    *Diameter.*—Approximately 15 cm.
    *Growth habit.*—Stemless.
    *Growth season.*—Flowers year round.
    *Temperature tolerance.*—Average temperatures of 20–22 C. are ideal, tolerant between 14 C. to 30 C.
    *Diameter.*—Approximately 15 cm.
Foliage:
    *Size.*—3–5.5 cm in length; 0.1–0.2 cm in width.
    *Shape.*—Lanceolate.
    *Surface texture.*—Smooth.
    *Color.*—Upper side RHS 137 A; lower side RHS 137 C.
Flowers:
    *Borne.*—Erect stalks.
    *Shape of inflorescence.*—Single head.
    *Length of stalk.*—Approximately 22–35 cm.
    *Number of stalks.*—Approximately 15–50 (depending on the size of the plant).

*Diameter of the inflorescence.*—Approximately 1 cm.
*Depth of the inflorescence.*—0.5 cm.
*Color of the inflorescence.*—Green-white, RHS 157A.
*Number of flowers per inflorescence.*—Approximately 100.
*Lastingness of the inflorescence.*—An individual inflorescence lasts approximately 10 weeks, the plant produces inflorescences for approximately 50 weeks.

Seeds:
*Quantity.*—Approximately 450–600 seeds per plant (depending on plant size).
*Diameter.*—0.1 mm.
*Color.*—Yellow/light-brown.
*Shape.*—Oval.

We claim:

1. A *Syngonanthus chrysanthus* plant designated cultivar 'Mikado' obtained from seed having American Type Culture Collection (ATCC) deposit accession no. PTA-4765.

2. *Syngonanthus chrysanthus* seed having ATCC deposit accession no. PTA-4765.

3. A *Syngonanthus chrysanthus* plant produced from the seed of claim 2.

4. Plant parts obtained from the *Syngonanthus chrysanthus* plant of claim 3.

5. A method of producing new *Syngonanthus chrysanthus* varieties comprising the step of (a) crossing *Syngonanthus chrysanthus* 'Mikado,' produced from seed accorded ATCC accession no. PTA-4765, as a male or female parent, with another *Syngonanthus chrysanthus* plant and (b) selecting progeny.

* * * * *